United States Patent [19]

Cooke

[11] 4,182,638

[45] Jan. 8, 1980

[54] COATING PROCESS WITH VOLTAMMETRIC SENSING OF THE COATING SOLUTION

[75] Inventor: Brian A. Cooke, Knotty Green, England

[73] Assignee: Imperial Chemical Industries Limited, England

[21] Appl. No.: 810,354

[22] Filed: Jun. 24, 1977

[30] Foreign Application Priority Data

Jun. 28, 1976 [GB] United Kingdom ............... 26797/76

[51] Int. Cl.² .......................... C23F 7/10; C23C 3/00
[52] U.S. Cl. ........................... 148/6.15 R; 148/6.15 Z; 427/8; 427/345; 427/436; 118/690; 204/1 T
[58] Field of Search ................. 427/8, 345, 436, 437; 148/6.15 Z; 324/30 R, 30 B; 118/7, 11; 137/5; 204/1 T

[56] References Cited

U.S. PATENT DOCUMENTS

| | | | |
|---|---|---|---|
| 2,805,191 | 9/1957 | Hersch .................................. | 204/1 Y |
| 2,864,750 | 12/1958 | Hughes et al. ........................ | 204/149 |
| 2,888,640 | 5/1959 | Eckfeldt et al. ..................... | 324/30 B |
| 3,025,459 | 3/1962 | Eckfeldt et al. ..................... | 324/30 B |
| 3,061,773 | 10/1962 | Ellison et al. ........................ | 324/30 R |
| 3,250,689 | 5/1966 | Seyl ....................................... | 324/30 R |
| 3,329,587 | 7/1967 | Steinbrecher et al. ............... | 204/1 T |
| 3,350,284 | 10/1967 | Steinbrecher et al. ............... | 204/1 T |
| 3,369,928 | 2/1968 | Arlow .................................. | 148/6.15 Z |
| 3,470,465 | 9/1969 | Wuschke ............................. | 324/30 B |
| 3,515,094 | 6/1970 | McVey ................................. | 118/7 X |
| 3,532,519 | 10/1970 | Hirohata et al. ..................... | 427/437 X |
| 3,934,054 | 1/1976 | Schmeling ............................ | 427/437 X |
| 4,089,710 | 5/1978 | Cooke .................................. | 148/6.15 R |

OTHER PUBLICATIONS

Kirk–Othmer, Encyclopedia of Chemical Technology, 2nd Ed., 1965, vol. 7, p. 762.

*Primary Examiner*—Ralph S. Kendall
*Attorney, Agent, or Firm*—Cushman, Darby & Cushman

[57] ABSTRACT

The effective concentration of an electroactive ingredient of a coating solution is determined, and may be restored to a desired level, in response to deviations in the voltammetric current sensed at an indicating electrode comprised of a noble metal.

18 Claims, No Drawings

COATING PROCESS WITH VOLTAMMETRIC SENSING OF THE COATING SOLUTION

This invention relates to a process of coating a metal substrate by reaction of the substrate with a coating solution wherein a constituent of the solution can be maintained at a desired concentration; to a method of sensing such a constituent; and to apparatus suitable for sensing the constituent and optionally capable of holding its concentration at a desired level.

It is frequently required to coat a metal substrate by chemical reaction of the substrate with a suitable coating solution in order, for example, to improve the corrosion resistance, the appearance or the handling properties of the metal. Typical of such coating processes are those in which there is applied to a metal substrate a metal phosphate coating or a copper metal coating. The control of the quality of coatings obtained by these and other processes often depends upon the control of the concentration in the coating solution of one or more constituents which are depleted or enriched in the solution as the process proceeds. Typical constituents whose concentration may require to be controlled include nitrite (added to the solution for example as sodium nitrite), cupric ions (added for example as copper sulphate), hydrogen, peroxide, zinc ions, protons and dissolved iron. Accurate control of the concentration of such constituents may be difficult to achieve and often relies upon a periodic manually performed chemical analysis of the solution as a result of which suitable correction of the composition of the solution is made.

In certain processes for coating metal substrates, the concentration of a constituent in a coating solution which is reacted with the substrate is sensed by the measurement of an electrochemical characteristic of the solution. Thus, for example, the conductivity of the solution may be measured and a suitable proportion of an appropriate ingredient added to the solution until the conductivity returns to a desired value. It can readily be contrived that such additions to restore conductivity are made automatically. Another method of control, readily capable of automation, depends upon the measurement of the electrical potential between a redox electrode and a reference electrode immersed in the coating solution. In one such prior method, described in British Pat. No. 1,113,270, for maintaining the concentration of nitrite in a solution which is used in a process for applying a zinc phosphate coating to a succession of ferrous metal surfaces, the solution is replenished with nitrite ion at a rate governed by the potential measured between a redox electrode and a reference electrode immersed in the solution. Experience over a wide range of plant conditions has shown that, whilst this method is satisfactory when the ferrous metal surfaces are being treated under conventional conditions and in a regular manner, it is less satisfactory when the work rate is low or when there are fluctuations in the throughput.

In another method (capable of automation and described in British Pat. No. 1,011,177) for measuring the fluoride activity of an aqueous fluoride-containing solution, particularly such a solution which is used in the treatment of a metal substrate by reaction with the metal, there is measured the electric current which flows between an indicating anode composed at least partially of p-type silicon and a cathode inert with respect to the solution being tested when these electrodes are connected to a direct current source. This voltammetric technique relies for its success on the special characteristics of the p-type silicon semi-conductor electrode. We are unaware of any more general applications of voltammetric techniques to the analysis and control under plant conditions of metal pretreatment solutions or the like. Probable reasons for this lack of application are:

(a) the common use in voltammetry of a supporting electrolyte to suppress electromigration by the constituent in question and thus to render the diffusion current obtained an accurate indication of the concentration of that constituent; it would be preferable in a continuously operated device to avoid adding supporting electrolyte;

(b) the fact that metal pretreatment solutions are commonly metastable or unstable in regard to species in solution or suspension and may, therefore, rapidly form undesirable coatings on sensing electrodes immersed therein;

(c) the dropping mercury electrode (which is widely used in voltammetry) is poorly suited, on grounds of fragility and difficulties of maintenance, to use under the rigorous conditions of metal pretreatment plants; in addition, it can be used over only a limited range of potential difference with respect to the solution;

(d) the difficulty in finding electrode materials having the required consistency of behaviour to function reproducibly in metal pretreatment solutions over a long period of time.

We have now found that in a coating process wherein a metal substrate is coated by reaction of the metal with a coating solution the effective concentration of an electroactive constituent of the coating solution can be sensed and its concentration adjusted to a desired level by suitable means (for example, by addition of a suitable ingredient) in response to the magnitude of electrical current which flows between an indicating electrode comprised of a noble metal and a counter-electrode immersed in the coating solution; conditions of potential appropriate to the electroactive constituent being established at the indicating electrode with reference to the neighbouring solution or to a suitable reference electrode immersed therein. Such sensing of the current flow at an indicating electrode is herein referred to and is understood by those skilled in the art as "voltammetry".

By "an electroactive constituent" we mean a constituent taking part in an electrode reaction at a definite electrode potential or within a definite electrode potential range, giving rise to a current whose magnitude is a function of the concentration of that constituent. Examples of electroactive constituents relevant to metal pretreatment are nitrite, copper ions, peroxide, zinc ions and protons.

By "the effective concentration" we mean the concentration of the constituent which governs its function in the coating process.

The relationship between the current due to the electrode reaction and the effective concentration of the electroactive constituent is a function of the geometry, including the area and physical disposition, of the indicating electrode and may also be affected by hydrodynamic conditions in the solution tested. In order to stabilise this relationship, it is thus necessary to maintain constant geometry of the indicating electrode and to control hydrodynamic conditions in the solution tested. Control of the hydrodynamics of the solution tested may include maintaining it in an essentially static condition or establishing a definite pattern of flow of solution relative to the indicating electrode.

According to one aspect of the present invention we provide a method of sensing the effective concentration of an electroactive constituent of a coating solution reactive with a metal substrate which comprises the step of sensing said constituent voltammetrically at an indicating electrode comprised of a noble metal.

According to another aspect of the invention we provide a process of applying a coating to a metal substrate by reaction of the metal with a coating solution which comprises at least one electroactive constituent and wherein the effective concentration of the electroactive constituent in the coating solution is sensed voltammetrically at an indicating electrode comprised of noble metal, the concentration of the electroactive constituent in the coating solution being subsequently adjusted in response to deviations in the voltammetric current from an optimum value.

Preferably, and most conveniently, the indicating electrode is comprised of platinum, but may comprise gold, iridium, osmium, palladium, rhodium or ruthenium, or alloys thereof.

In order to maintain the indicating electrode in that condition which is most suitable for sensing the electroactive constituent voltammetrically it is preferred to clean the said electrode periodically. When the indicating electrode forms part of an automated system, cleaning is preferably effected by a step which makes the indicating electrode one electrode, generally an anode, in an electrolytic cell and by passing electrical current for an appropriate period of time such that deposits tending to form on the indicating electrode are substantially eliminated. The electrolyte in such an electrolytic cleaning cell can most conveniently comprise the coating solution or a sample thereof.

The conditions of potential at the indicating electrode are regulated with reference to the solution most effectively with the aid of a reference electrode and using a suitable external electrical circuit such that the sign and magnitude of the potential are appropriate to the electroactive constituent to be sensed.

The voltammetric current thus passes in an electrolytic cell containing the coating solution between the indicating electrode and a counter-electrode in the same cell. Said cell may consist of the tank in which the coating solution is retained during operation or may be a separate smaller container fed continuously or intermittently with coating solution drawn from the tank. The counter-electrode may function as a reference electrode to accomplish the definition of the required potential condition of the indicating electrode, or a third electrode may be employed as reference electrode. A suitable choice for such a third electrode is, for example, the calomel reference electrode which may be arranged to contact the solution in the vicinity of the indicating electrode by means of a suitable liquid junction, e.g. the well-known saturated potassium chloride salt bridge. Because substantial currents cannot be drawn through such a reference electrode assembly, it can be connected in the external electrical circuit to the indicating and counter-electrodes by means of a potentiostatic device. The potentiostatic device is contrived to ensure that the voltammetric current which passes between indicating and counter-electrodes is that which establishes the potential difference between indicating and reference electrodes at the required definite value, said value being selected as appropriate to the electroactive constituent under investigation. The reference electrode thus acts as an indicator of the potential of the solution in the vicinity of the indicating electrode.

The adoption of a separate reference electrode simplifies the selection of the counter-electrode in such respects as material of construction, geometry including size, location in the cell and surface condition. It is necessary only that the counter-electrode be of a material which is resistant to the coating solution and of sufficient area to pass the voltammetric current. Suitable materials include mild or stainless steel when the coating solution is a zinc phosphating solution. In the case in which the voltammetric cell is formed within the tank retaining the operating solution, the counter-electrode may consist of the tank wall if of metal. Highly acidic solutions, e.g. those employed in chemical coppering processes, require the selection of acid-resistant electrode material for the counter-electrode.

According to another aspect of the invention, we provide an apparatus for sensing the concentration of an electroactive constituent of a coating solution which comprises a cell suitable for containing the coating solution, an indicating electrode comprised of a noble metal, a counter electrode, optionally a reference electrode, means for applying a voltammetrically appropriate potential at the indicating electrode with reference to the counter-electrode or to the reference electrode, means for periodically releasing said potential and means for then applying a different potential between the indicating electrode and the counter electrode or the reference electrode for such time that deposits tending to form on the indicating electrode are substantially eliminated.

The potential at the indicating electrode which is appropriate to an electroactive constituent is established following conventional procedures; for example by adjustment of a potentiostat located in a circuit comprising a source of direct current, the indicating electrode and the reference electrode. The voltammetric current which flows between the indicating electrode and the counter electrode under the conditions of potential appropriate to an electroactive constituent which it is desired to sense may be determined, for example, by an ammeter located in a circuit comprising the indicating and counter electrodes.

The process of coating metal substrates, the method of sensing an electroactive constituent and the apparatus for use in such process and method all described herein may be adapted for use with a wide range of coating solutions which comprise an electroactive constituent. Particularly suitable processes which may be improved by the present invention include for example:

(a) A process of coating metal substrates by reaction of the substrate with an aqueous acidic metal phosphate solution. Preferably the metal phosphate is zinc phosphate. In such a process the substrate is coated with a metal phosphate.

(b) A process of coating a ferrous metal substrate with copper by reaction of the substrate with a solution containing copper sulphate, for example an aqueous solution comprising copper sulphate, sulphuric acid and a substance which inhibits acid attack on the ferrous metal substrate.

In processes of type (a) electroactive constituents which may be sensed include:

(1) nitrous acid which may be present in the acid solution to accelerate the coating process and which is usually replenished in the coating solution by addition of a nitrite, for example, sodium nitrite. In a coating solution which comprises acidic zinc phosphate and optionally nitrate, chlorate and sodium ions, nitrous acid may be sensed, for example, at a platinum indicating electrode potential, with respect to the saturated calomel electrode (SCE), of +0.7 to +1.4 volts. A particularly suitable potential is +1.05 volts. Electrolytic cleaning of the indicating electrode may be effected by the application of +1.8 volts, with respect to the SCE for periods of the order of 15 seconds, or greater.

(2) the free acidity (e.g. as indicated in a conventional titration against alkali using methyl orange as indicator) of the coating solution which may be sensed when the indicating electrode has a potential with respect to the SCE in the range −0.60 to −1.10 volts.

(3) the zinc ion present in a coating solution comprising acid zinc phosphate when the indicating electrode has a potential with respect to the SCE in the range −1.20 to −1.50 volts. A particularly suitable potential is −1.25 volts.

(4) hydrogen peroxide, when the indicating electrode should have a potential in the region of +0.7 to 1.4 (e.g. 0.95) volts.

A particularly suitable electroactive constituent which may be sensed in process (b) is ionic copper. When the coating solution comprises copper sulphate and sulphuric acid, the copper ion may be sensed at an indicating electrode potential with respect to the SCE of 0 to −0.50 volts. A particularly suitable potential is −0.39 volts.

A convenient and satisfactory method of carrying out the invention consists of establishing the voltammetric potential difference at a set instant in time and maintaining its value steady for some time thereafter. During this period of voltammetric current may fluctuate in value, e.g. decrease as time passes, and may or may not ultimately become steady. We have found the value of current reached after a period of 5 seconds or more to be a satisfactory indication of the effective concentration of the electroactive constituent, and the invention is best carried out by selecting a definite time after the establishment of the voltammetric potential difference and observing the voltammetric current always at that time (or relaying its value at that time to a comparison circuit capable of initiating an appropriate adjustment in composition). Suitable times after establishment of the voltammetric potential difference are between 2 and 120 seconds, preferably in the range 15-30 seconds.

Whilst the conditions of potential established at the indicating electrode appropriate to the sensing of a particular electroactive constituent are not limited and may, for example, comprise a steady potential or a cyclically varying potential, the instrumentation of the voltammetric system is rendered convenient if a steady potential is chosen.

In a preferred process according to the invention wherein a coating solution is reacted with a metal substrate the concentration of an electroactive constituent of the coating solution is maintained at a desired level by carrying out the steps: (a) establishing at an indicating electrode comprised of a noble metal, which is at least partly immersed in the coating solution or in a sample thereof, conditions of potential appropriate to the electroactive constituent and with reference to the solution or to a reference electrode at least partly immersed therein, (b) sensing at a chosen instant after the commencement of (a) the voltammetric current which flows under the conditions of potential between the indicating electrode and a counter electrode at least partly immersed in the solution, and (c) adjusting the composition of the coating solution in response to a deviation of the voltammetric current from an optimum value.

Step (c) may, optionally, be initiated automatically.

The invention is illustrated by the following Examples in which parts and percentages are by weight:

EXAMPLE 1

This Example describes a process of applying a zinc phosphate coating to steel panels using a phosphating solution which comprised as constituents zinc, phosphate, nitrate and nitrite. The effective concentration of the electroactive nitrite constituent was periodically sensed voltammetrically (as nitrous acid) and further nitrite was added to the solution as the voltammetric current fell below the value obtained when the bath was initially made up.

A coating solution of pointage 20-25 was prepared from a concentrate which consisted of:

| | |
|---|---|
| Zinc oxide | 17.7% by weight, |
| 59% nitric acid | 34.5% by weight, |
| 81% phosphoric acid | 23.1% by weight, |
| and Water | 24.7% by weight, |

135 ml. of this concentrate being diluted with 5,000 ml. water. Sufficient sodium nitrite was added to this solution to give a titration on an acidified 50 ml. sample of the solution of 2.9 ml. 0.1 N potassium permanganate. The coating solution was replenished, as coating of the panels proceeded, to hold the strength at 20 points using a concentrate which consisted of:

| | |
|---|---|
| Zinc oxide | 14.5% by weight |
| 59% nitric acid | 21.6% by weight |
| 81% phosphoric acid | 46.0% by weight |
| and Water | 17.9% by weight |

The coating solution was held at 70° C. in a coating bath and 4 steel panels (each of area 1.5 square feet) were coated in this solution per hour. The process was continued for 9 hours and during this time the voltammetric current due to the nitrite constituent of the solution was periodically sensed in a sample cell consisting of a chamber to contain a 120 ml. sample of the coating solution (withdrawn at regular intervals from the coating bath), a platinum indicating electrode (1.5 mm. length and 0.5 mm. diameter platinum wire), a standard calomel reference electrode fitted with a saturated potassium chloride salt bridge and a steel counter electrode (of 50 cm² exposed area). The electrodes were adapted to be connected into an electrical control circuit which enabled the following voltage/time sequence to be followed in the sample cell over a total sequence period of 5 minutes.

| Time (seconds) | Voltage (at indicating electrode relative to a reference electrode) |
|---|---|
| 0–20 | +1.8v |
| 20–25 | 0v |
| 25–45 | −0.9v |
| 45–105 | 0v (Sample received in cell) |
| 105–135 | +0.8v (After 27 seconds sense |

-continued

| Time (seconds) | Voltage (at indicating electrode relative to a reference electrode) |
|---|---|
| 135-300 | 0v voltammetric current) |

This sequence was repeated throughout the time of operation of the process and the coating solution was replenished automatically with a 10% by weight aqueous solution of sodium nitrite in response to deviations in the voltammetric current. During the process there was maintained in the coating solution an effective concentration of nitrite equivalent to 2.7±0.2 ml. of N/10 potassium permanganate per 50 ml. of the solution.

The steel panels were coated with a consistently satisfactory coating of zinc phosphate which could only have been obtained manually by frequent manual control.

EXAMPLE 2

In this Example is described the application of a copper metal coating to steel wire using a coppering solution comprising copper sulphate. The effective concentration of copper ion was controlled in response to the sensing of the voltammetric current at a platinum electrode at −0.30 volts relative to the SCE.

6,800 liters of a "coppering" solution comprising sodium chloride, copper sulphate, suphuric acid and an inhibitor, were employed at 60° C. in a coating bath to treat pickled steel wire at a rate of 470 square meters of wire surface/hour. The effective concentration of copper ion in the initial "coppering" solution was such that a 1.00 ml sample of the solution was equivalent to 4.3 ml. of 0.02 M ethylene diamine tetra acetic acid using Alizarin Yellow indicator. A replenishment material containing copper sulphate was added to the coating bath in response to measurement of the voltammetric current due to copper metal ion at −0.30 volts.

The process was continued over a period of 30 hours and during this time, at suitable intervals of time the voltammetric current due to the copper ion constituent was sensed in a sample cell similar to that used in Example 1 except that the counter electrode was of platinised titanium since the coating solution was strongly acid. The following voltage/time sequence was observed in the sample cell over a total period of 5 minutes, and the sequence was repeated throughout the time of operation of the process:

| Time (seconds) | Voltage (at indicating electrode) |
|---|---|
| 0-30 | +2.5v |
| 30-90 | 0v (sample received in cell) |
| 90-120 | −0.3v (After 28 seconds sense voltammetric current) |
| 120-300 | 0v |

Throughout the process the effective concentration of copper ion was maintained by automatic replenishment and 1.00 ml. of the solution was consistently equivalent to 4.3±0.2 ml. of 0.02 M EDTA.

The coppered steel wire obtained over the 30 hour period of the process was of consistently high quality.

EXAMPLE 3

In this Example it is shown that the process of this invention, when applied to a "coppering" solution, provides substantially consistent results even when theiron content of the solution is increased and when the temperature is lowered from optimum values.

A bath containing a freshly prepared "coppering" solution substantially as described in Example 2 was employed at 60° C. to coat degreased steel panels using the method of control of effective copper ion described in Example 2. The concentration of ferrous iron in the bath was increased by known amounts and the temperature of the bath was lowered, in successive steps, according to the following table. The concentration of copper was adjusted at each step to maintain constant the voltammetric current

| Temperature ° C. | Bath condition | Copper ion concentration (ml. titration) 0.02 M EDTA | Coating weight (g/m²) |
|---|---|---|---|
| 60 | Fresh bath | 4.4 | 6.36 |
| 60 | Fresh bath + 1% iron | 4.7 | 6.55 |
| 60 | Fresh bath + 2% iron | 5.0 | 6.50 |
| 60 | Fresh bath + 3% iron | 5.4 | 6.45 |
| 55 | Fresh bath + 3% iron | 5.8 | 6.56 |

Thus the coating weight on the coated panels remained substantially constant despite an increase in the ferrous iron concentration of the bath and a lowering of the working temperature.

EXAMPLE 4

This Example illustrates the application of voltammetry at a platinum indicating electrode, according to the invention, to the control of hydrogen peroxide concentration in a solution suitable for treating a ferrous substrate with a coating comprising zinc phosphate.

A zinc phosphating solution of the following composition in gram. mol. per liter was prepared and held at 31° C.

| Zinc | 0.069 |
|---|---|
| Phosphate | 0.138 |
| Nitrate | 0.087 |
| Sodium | 0.083 |

3% hydrogen peroxide solution was added to the above solution such that an acidified 50 ml sample of solution was equivalent to 4.0 ml 0.1 N potassium permanganate solution. The voltammetric current due to peroxide was sensed at regular intervals of 15 minutes in the same manner as described in Example 1, but with the following voltage/time sequence.

| time sequence Time (seconds) | Voltage (at indicating electrode relative to saturated calomel reference electrode) |
|---|---|
| 0-30 | +2.3v |
| 30-35 | 0v |
| 35-55 | −0.45v |
| 55-135 | 0v |
| 135-165 | +0.95v (after 20 sec., i.e. at 155 sec, sense voltammetric current) |
| 165-900 | |

The voltammetric current was determined under the above conditions with hydrogen peroxide content corresponding to 4.0 ml 0.1 N $KMnO_4$ on an acidified 50 ml sample. A quantity of ferrous sulphate solution was then added so as to depress the $KMnO_4$ titration to 1.8 ml. A fall of 56% was observed in the voltammetric current. The voltammetric sensing circuit was then linked to an automatic dosing device supplying 3% hydrogen peroxide solution to the phosphating solution under test. This device replenished the hydrogen peroxide automatically until the original voltammetric current was restored. When this replenishment was complete, an acidified 50 ml sample of the phosphating solution was found to be equivalent to 4.2 ml 0.1 N $KMnO_4$ solution.

What we claim is:

1. A process of applying a coating to a metal substrate by reaction of the metal with a coating solution which comprises at least one electroactive constituent which takes part in an electrode reaction at a definite electrode potential or within a definite electrode potential range, giving rise to a current whose magnitude is a function of the concentration of that constituent and wherein the effective concentration of the electroactive constituent in the coating solution is sensed voltammetrically at an indicating electrode comprised of noble metal, the concentration of the electroactive constituent in the coating solution being subsequently adjusted in response to deviations in the voltammetric current from an optimum value.

2. A method according to claim 1 wherein the indicating electrode is comprised of a metal selected from the group consisting of platinum, gold, iridium, osmium, palladium, rhodium, ruthenium, and alloys thereof.

3. A method according to claim 2 wherein the indicating electrode is comprised of platinum.

4. A method according to claim 1 wherein the indicating electrode is periodically cleaned.

5. A method according to claim 4 wherein the cleaning is effected by a step wherein the indicating electrode is made one electrode is an electrolytic cell and electrical current is passed for an appropriate period of time such that deposits tending to form on the indicating electrode are substantially eliminated.

6. A method according to claim 5 wherein the indicating electrode is made an anode in the electrolytic cell.

7. A method according to claim 1 wherein the conditions of potential at the indicating electrode are regulated with reference to the coating solution with the aid of a reference electrode, and using an external electrical circuit such that the sign and magnitude of the potential are appropriate to the electroactive constituent to be sensed.

8. A method according to claim 1 wherein a voltammetric current passes in an electrolytic cell containing the coating solution between the indicating electrode and a counter electrode in the said cell, the counter electrode constituting the reference electrode.

9. A method according to claim 1 wherein a voltammetric current passes in an electrolytic cell containing the coating solution between the indicating electrode and a counter electrode in said cell, a third electrode being employed as a reference electrode.

10. A method according to claim 9 wherein the third electrode is a calomel reference electrode.

11. A process according to claim 1 wherein the metal is reacted with an aqueous acidic metal phosphate solution.

12. A method according to claim 11 wherein the metal comprises a ferrous metal.

13. A process according to claim 11 wherein the electroactive constituent which is sensed voltammetrically in the coating solution is selected from the group consisting of nitrite, peroxide, zinc ions and protons.

14. A process according to claim 13 wherein the metal substrate comprises a ferrous metal.

15. A process according to claim 1 wherein a ferrous metal is reacted with a solution comprising copper sulphate and the electroactive constituent is ionic copper.

16. A method according to claim 15 wherein the metal substrate comprises a ferrous metal.

17. A process according to claim 1 which comprises the steps:
   (a) establishing at the indicating electrode comprised of a noble metal, which is at least partly immersed in the coating solution or in a sample thereof, conditions of potential appropriate to the electroactive constituent and with reference to the solution or to a reference electrode at least partly immersed therein
   (b) sensing at a chosen instant after the commencement of (a) the voltammetric current which flows under the conditions of potential between the indicating electrode and a counter electrode at least partly immersed in the solution, and
   (c) adjusting the composition of the coating solution in response to a deviation of the voltammetric current from an optimum value.

18. A process according to claim 17 wherein step (c) is initiated automatically.

* * * * *